(12) United States Patent
Streit et al.

(10) Patent No.: US 8,398,594 B2
(45) Date of Patent: Mar. 19, 2013

(54) SPRING ARRANGEMENT IN AN INJECTION DEVICE

(75) Inventors: Ursina Streit, Bern (CH); Markus Bollenbach, Bern (CH); Patrick Hostettler, Hasle-Ruegsau (CH); Daniel Kuenzli, Langendorf (CH)

(73) Assignee: TecPharma Licensing AG, Burgdorf (CH)

( * ) Notice: Subject to any disclaimer, the term of this patent is extended or adjusted under 35 U.S.C. 154(b) by 55 days.

(21) Appl. No.: 12/563,805

(22) Filed: Sep. 21, 2009

(65) Prior Publication Data

US 2010/0137798 A1 Jun. 3, 2010

Related U.S. Application Data

(63) Continuation of application No. PCT/CH2008/000119, filed on Mar. 19, 2008.

(30) Foreign Application Priority Data

Mar. 22, 2007 (DE) .......................... 10 2007 013 837

(51) Int. Cl.
*A61M 5/20* (2006.01)
*A61M 5/32* (2006.01)
(52) U.S. Cl. .......................... 604/136; 604/135; 604/198
(58) Field of Classification Search .................. 604/110, 604/134–139
See application file for complete search history.

(56) References Cited

U.S. PATENT DOCUMENTS

| 3,797,489 A | 3/1974 | Sarnoff | |
|---|---|---|---|
| 5,545,144 A * | 8/1996 | Fryklund et al. | 604/187 |
| 6,149,626 A | 11/2000 | Bachynsky et al. | |
| 6,387,078 B1 | 5/2002 | Gillespie, III | |
| 2003/0093036 A1* | 5/2003 | Crossman et al. | 604/197 |
| 2003/0103430 A1 | 6/2003 | Kim et al. | |
| 2003/0105430 A1* | 6/2003 | Lavi et al. | 604/136 |
| 2004/0215151 A1* | 10/2004 | Marshall et al. | 604/198 |

FOREIGN PATENT DOCUMENTS

| DE | 20 2007 000578 U1 | 3/2007 |
|---|---|---|
| EP | 0 516 473 B1 | 2/1996 |
| EP | 1 503 816 B1 | 1/2007 |
| EP | 1 743 666 A | 1/2007 |
| WO | WO 99/03529 A | 1/1999 |
| WO | WO 2005/115511 A | 12/2005 |
| WO | WO 2006057636 A1 * | 6/2006 |

* cited by examiner

*Primary Examiner* — Nicholas Lucchesi
*Assistant Examiner* — Jenna Zhang
(74) *Attorney, Agent, or Firm* — Dorsey & Whitney LLP; David E. Bruhn, Esq.

(57) ABSTRACT

An injection device, in some embodiments an autoinjector, which includes a thrust spring that advances an injection needle from an initial position to an insertion position from the distal end of the injection device and that causes a product to be emptied from the product reservoir by an emptying movement, and a return spring that retracts the injection needle from the insertion position into the distal end of the injection device counter to the force of the thrust spring, wherein the return spring is decoupled from the thrust spring during the emptying movement.

14 Claims, 13 Drawing Sheets

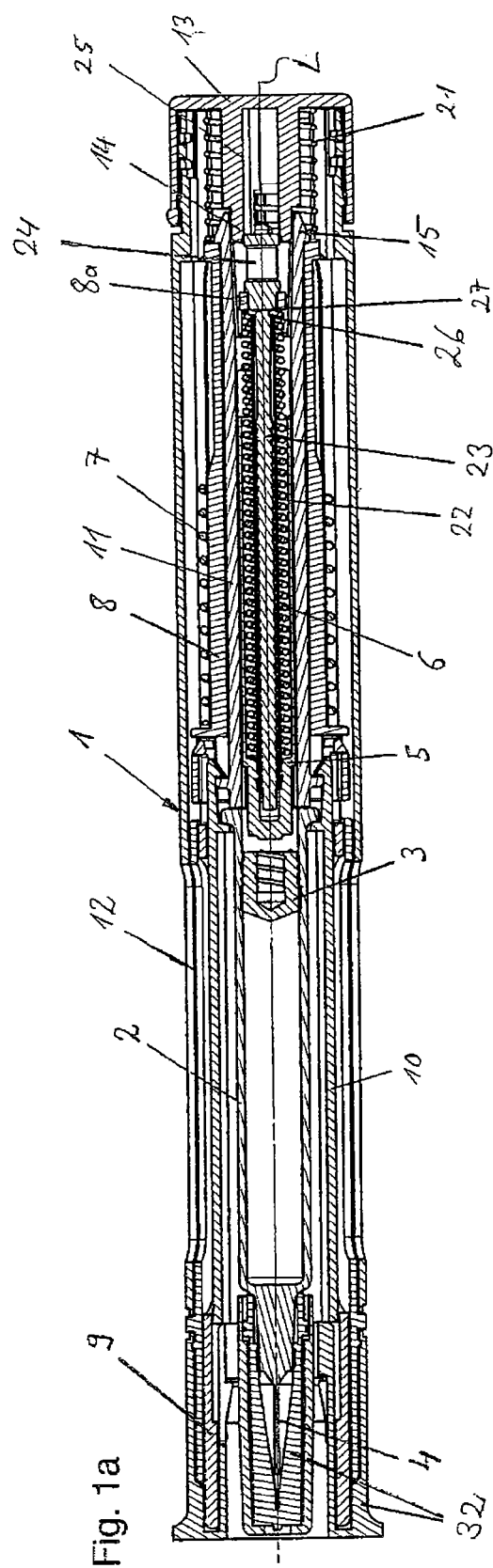
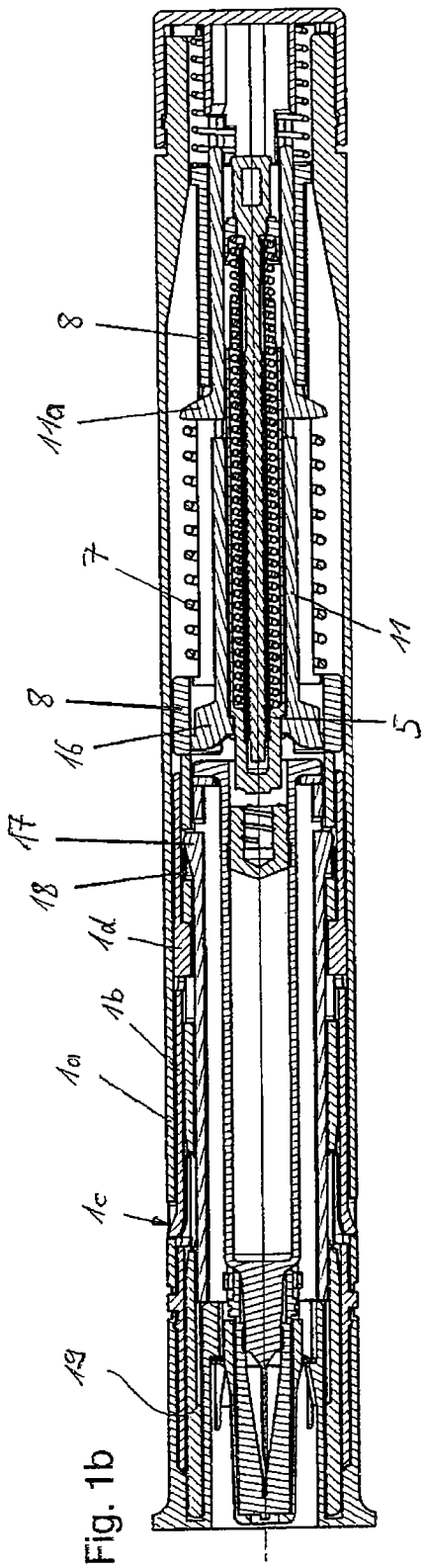
Fig. 1a
Fig. 1b

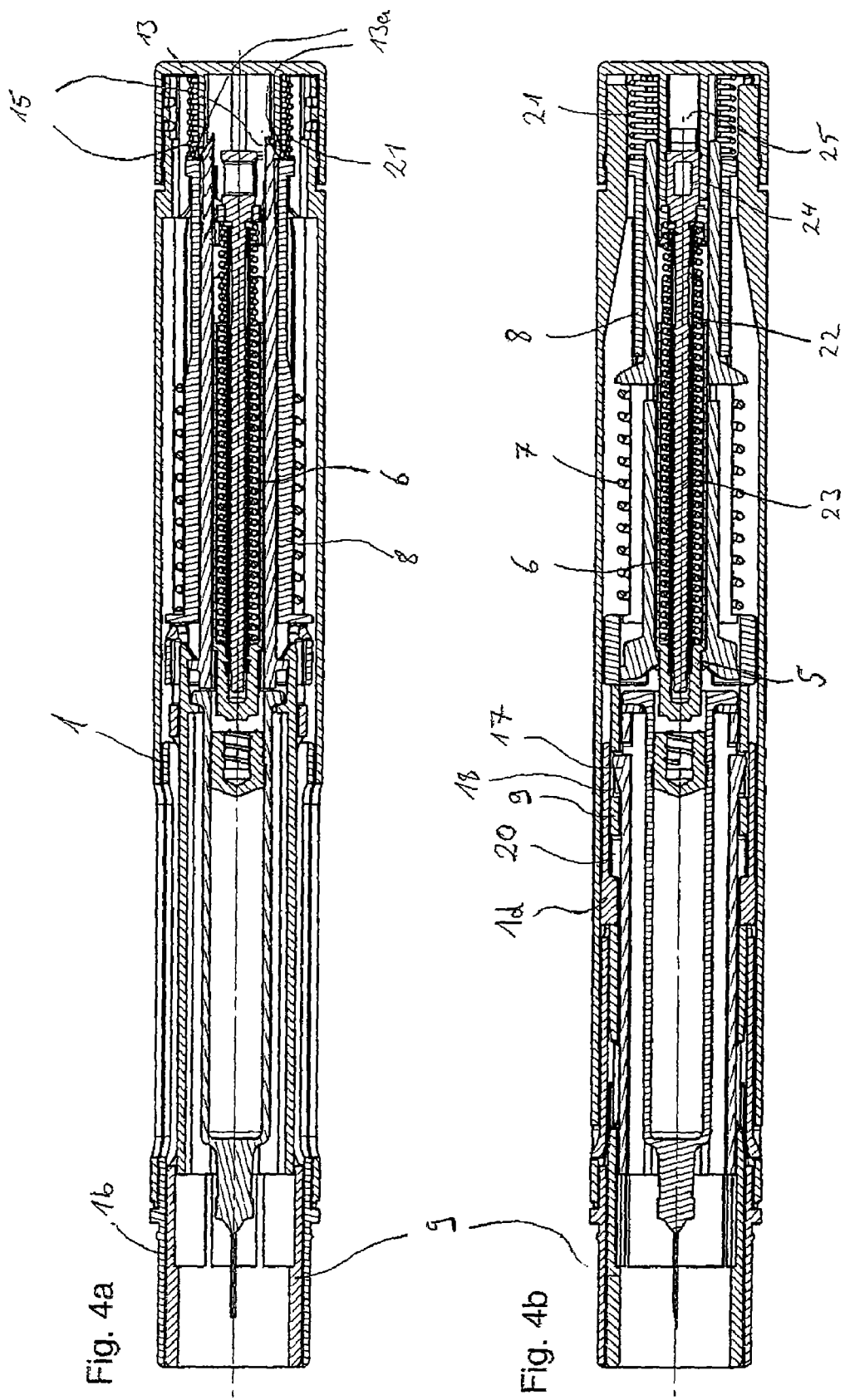

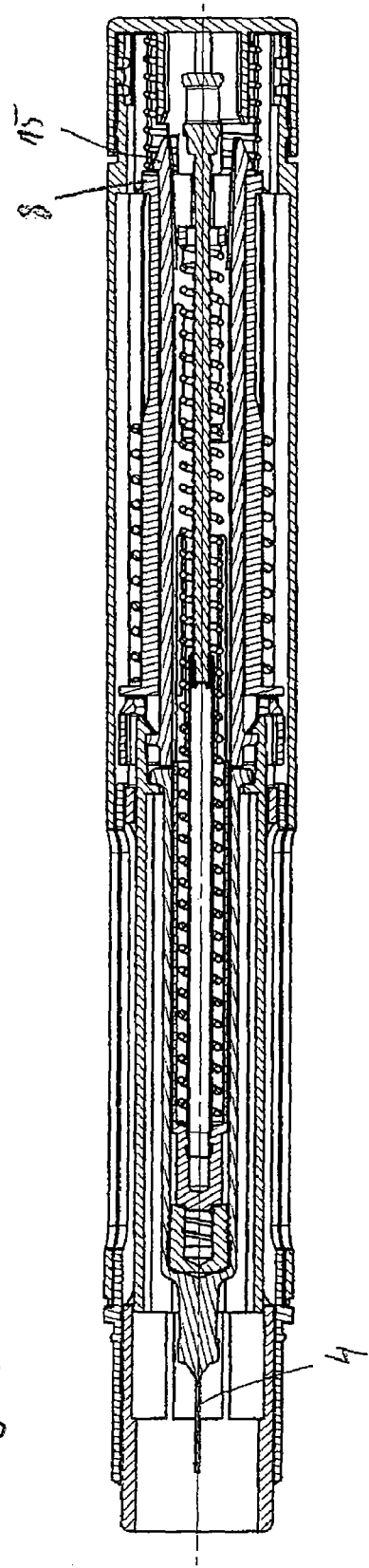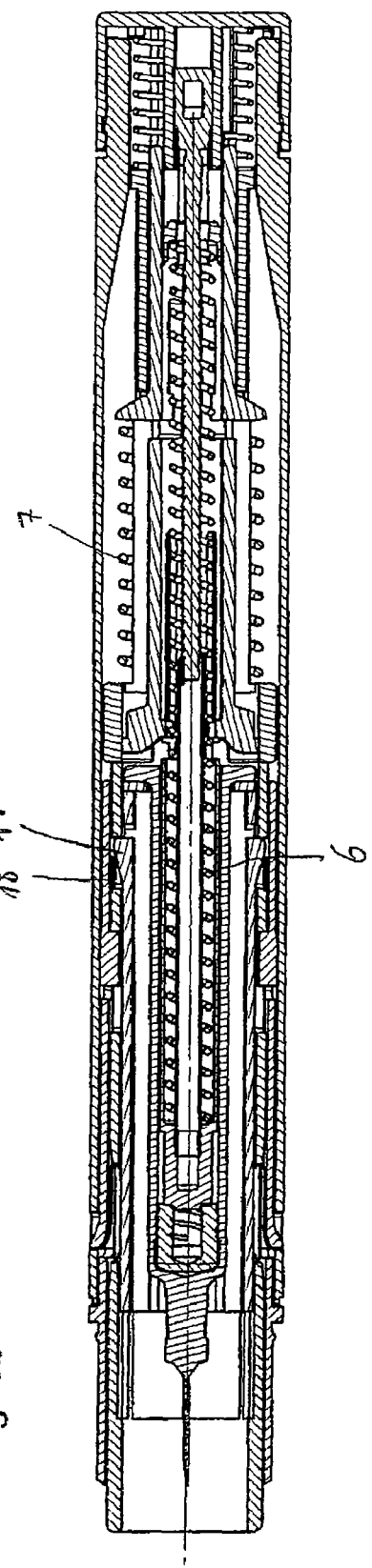
Fig. 9a
Fig. 9b

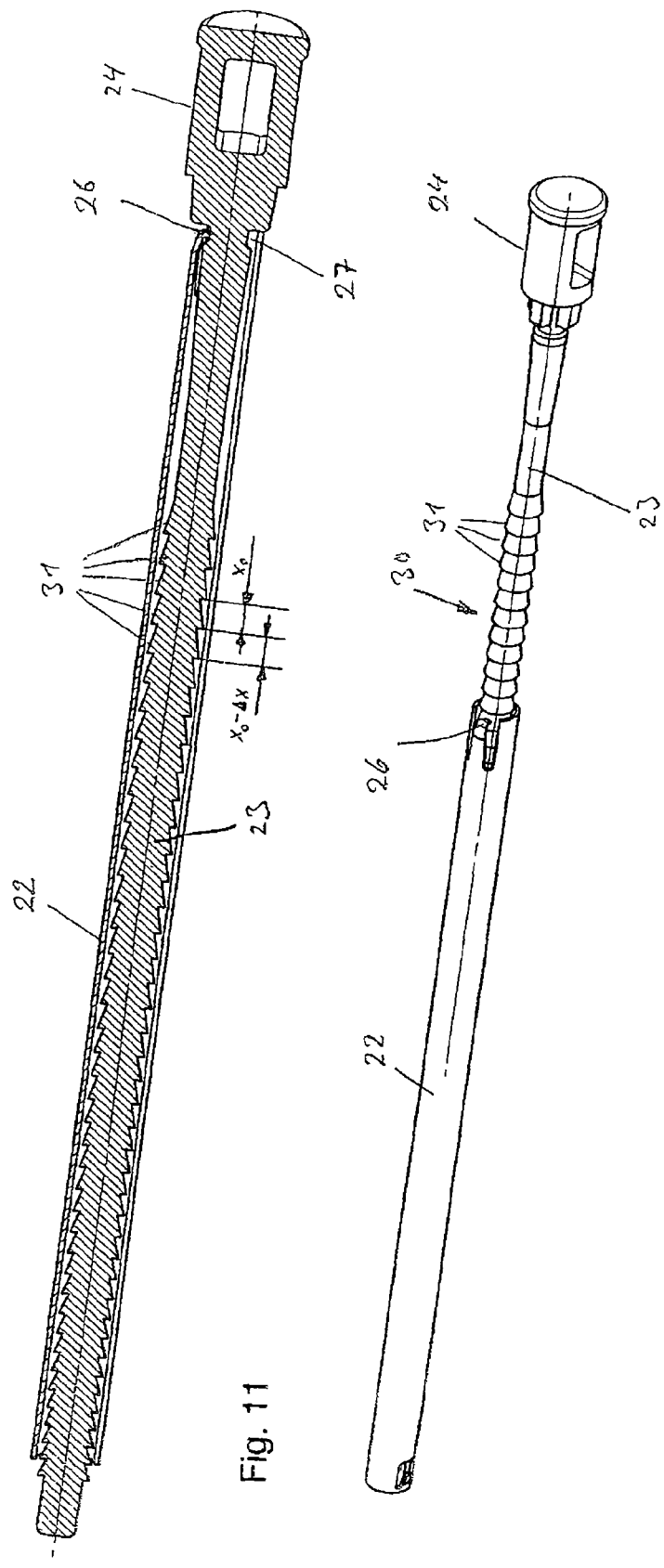

SPRING ARRANGEMENT IN AN INJECTION DEVICE

CROSS-REFERENCED RELATED APPLICATIONS

This application is a continuation of International Patent Application No. PCT/CH2008/000119 filed Mar. 19, 2008, which claims priority to German Patent Application No. DE 10 2007 013 837.9 filed Mar. 22, 2007, the entire content of both of which is incorporated herein by reference.

BACKGROUND

The present invention relates to device for injecting, infusing, delivering, administering or dispensing a substance, and to methods of making and using such devices. More particularly, it relates to the field of injection devices, including automatic injection devices or autoinjectors, for administering a liquid product, e.g. a medicinal or therapeutic substance or product or a medicament.

U.S. Pat. No. 3,797,489 discloses an injection device comprising a driving spring acting on a product container or a plunger of the product container and a spring opposing the driving spring via the product container. The opposing spring has three functions, that of acting as a damper, a safety mechanism and a moving the needle back by a short amount. The driving spring is coupled with the opposing spring during both the injection process via a fixed coupling with the product container and during the dispensing movement via the liquid of the product container. In the case of this device, the task of balancing the spring forces represents a major challenge.

EP 0 516 473 B1, EP 1 503 816 B1 and U.S. Pat. No. 6,387,078 each disclose injection devices in which the driving spring is uncoupled from the return spring after the product has been dispensed, i.e. after the dispensing movement has ended to retract the injection needle.

SUMMARY

An object of the present invention is to provide an injection device and a method of operating such an injection device which provides an advantageous process of dispensing the product.

The invention relates to an injection device for administering what is preferably a liquid product, such as a medicament for hormone treatment or diabetes treatment, for example. In particular, the injection device may be an automatic injector. In the case of an automatic injector, a mechanism for example may be provided which enables automatic piercing by the needle, followed by dispensing of the product. By preference, the needle is also retracted into the automatic injector automatically, in which case it may be desirable for the user of the device to effect another manipulation for this purpose.

In one embodiment, the present invention comprises an injection device, in some embodiments an autoinjector, which comprises a thrust spring that advances an injection needle from an initial position to an insertion position from the distal end of the injection device and causes a product to be emptied from the product reservoir by an emptying movement, and a return spring that retracts the injection needle from the insertion position into the distal end of the injection device counter to the force of the thrust spring, wherein the return spring is decoupled from the thrust spring during the emptying movement.

In some embodiments, the present invention comprises an injection device, e.g. an autoinjector, which comprises a thrust spring which advances an injection needle from an initial position to an insertion position from the distal end of the injection device and which allows a product to be emptied from the product reservoir by way of an emptying movement, and a return spring that retracts, e.g. completely, the injection needle from the insertion position into the distal end of the injection device counter to the force of the thrust spring, wherein the return spring is decoupled from the thrust spring during the emptying movement.

In some embodiments, the injection device comprises a driving spring, by which an injection needle can be moved forward (distally) out of the distal end of the injection device from an initial position into a piercing position and by which a product can be dispensed from a product container due to a dispensing movement. The driving spring may be, for example, a spiral coiled spring which can be tensed to a pressure, and may be made from spring steel or some other appropriate metal, for example. In principle, plastic springs or rubber-elastic springs would also be suitable as a driving spring. The driving spring may be supported at one end, e.g. the proximal (rear) end, on a housing of the injection device or another element which is axially stationary or displaceable relative to the housing. Such a displaceable element might be a switch sleeve, for example. The driving spring may be supported on a plunger rod at its other, distal end. The plunger rod may be at least approximately sleeve-shaped, in which case the driving spring may be disposed at least partially in the sleeve-shaped part so that the sleeve-shaped part at least partially surrounds the spring. To generate a piercing movement, the driving spring may be coupled with the needle so that the latter effects the piercing movement, i.e. moves forward out of the distal end of the device and into a piercing position. The amount by which the needle extends out beyond the distal end of the device corresponds to the piercing depth of the needle. For example, the driving spring may be coupled with the needle via the plunger rod, which is connected to a drive structure in an axially fixed arrangement during the piercing movement. The drive structure may comprise and be thought of and/or referred as being made up of the product container, a holder for the product container and/or a function sleeve in which the plunger rod is accommodated, for example. The needle is disposed on the distal end of the product container, and has a fluid connection to the interior of the product container. At the proximal end of the product container, the product is closed off by a plunger which is able to move relative to the product container. When the plunger is pushed in the direction of the needle, the product is dispensed.

To dispense product, i.e. to generate a dispensing movement, the driving spring may act on the plunger via the plunger rod, for example. In some preferred embodiments, the dispensing movement ends when the plunger makes contact with the distal end of the product container.

In some preferred embodiments, the injection device also has a return spring, by which the injection needle can be retracted from the piercing position into the distal end of the injection device against the force of the driving spring. The needle can be fully retracted because this minimises the risk of injury to a user of the device or third parties. Since the return spring acts against the force of the driving spring to this end, the driving spring and return spring are coupled. The return spring may be of a construction similar to that of the driving spring. The return spring may surround the driving spring, for example. The return spring may be coupled with the needle via the drive structure, for example. The return spring is supported on the function sleeve by its proximal end and thus acts on the drive structure, the parts of which are connected to one another in an axially fixed arrangement. In some preferred embodiments, the return spring may be disposed proximally of the product container, although this does not rule out the possibility of disposing the return spring distally of the product container.

In some preferred embodiments, the return spring is uncoupled from the driving spring during the dispensing movement. Coupling as used in this context is intended to mean that the springs exert forces to one another and can be mutually tensed. Conversely, uncoupled springs are not able to transmit forces to one another. An advantage of an injection device in accordance with the present invention is that because of the coupling, the driving spring does not act against the force of the return spring, which means that the product is dispensed from the product container more effectively.

In some preferred embodiments, the return spring and driving spring are coupled for the retracting movement and/or for the driving movement, i.e. for the piercing movement of the injection needle. An advantage of this is that, due to the coupling, the force resulting from the sum of the force vectors of the individual springs is relatively low, thereby reducing the stress to which the injection device is subjected as the needle pierces or is retracted. This also reduces the risk of malfunction or even breakage of the device due to excessive driving forces. To retract the injection needle, the driving spring can be tensed by the return spring. Alternatively or in addition, the return spring can be tensed by the driving spring to drive the injection needle forward. For example, the driving spring is coupled with the return spring via a function sleeve during the piercing movement effected via the plunger rod, which engages with a lock element disposed on the function sleeve and is therefore axially fixed relative to the function sleeve. To retract the needle after dispensing product, the return spring is coupled with the driving spring, e.g. via the function sleeve, due to the product container connected to it in an axially fixed arrangement with the plunger standing distally out from it. During the retracting movement, the return spring relaxes and thus tenses the driving spring. During the piercing movement, the driving spring relaxes and thus tenses the return spring. This mutual tensing ability is generated due to the fact that the return spring is uncoupled from the driving spring during the dispensing movement because the return spring maintains its pre-tensioning in the uncoupled state, while the driving spring is able to continue relaxing as the product is dispensed. The spring force of the driving spring decreases when subjected to the spring force of the return spring, which remains tensed as the product is dispensed.

In some preferred embodiments, the spring force of the return spring for retracting the injection needle is stronger than the spring force of the driving spring, and/or the spring force of the driving spring causing the piercing movement of the injection needle is stronger than the spring force of the return spring.

In some preferred embodiments, an injection device in accordance with the present invention comprises a lock element, which can be moved radially into a locked engagement, e.g. into a cut-out, to uncouple the driving spring and return spring. This being the case, the injection needle is axially secured and the return spring is maintained in a tensed state. The cut-out may be disposed in a housing or an element fixedly secured to the housing, for example. The cut-out is disposed in an operating sleeve which can be moved along the longitudinal axis relative to the housing of the device. The operating sleeve can be placed on the injection site of the patient at its distal end, as a result of which it moves in the proximal direction relative to the housing. The movement of the operating sleeve in the proximal and distal direction triggers specific switching operations in the injection device.

In some embodiments, the lock element may be provided on the function sleeve, for example. In some preferred embodiments, the lock element is joined to the function sleeve, e.g. integrally, via a resilient arm. The lock element is biased so that it tends to locate in the cut-out. When the lock element is located in the cut-out, the function sleeve via the lock element, the operating sleeve and a switch sleeve sitting in contact with the operating sleeve constitute a fixed clamp for the return spring. Accordingly, the force is able to flow from the proximal end of the return spring via this clamp to the distal end of the return spring.

In some preferred embodiments, the same or a different lock element releasably engages with the plunger rod, in which case when the engagement is released, the driving spring which can be driven by the plunger rod is able to move relative to the lock element and push the plunger of the product container in the direction of the outlet of the product container. If another lock element is provided, it, like the other lock element, may be disposed on the function sleeve. The plunger rod causes a relative movement with respect to the function sleeve as the product is dispensed.

In the case of a preferred embodiment in which the lock element is provided both to locate in a cut-out and to engage in the plunger rod, the lock element is unlatched from the plunger rod and releases it with a view to dispensing product approximately at the same time as the lock element engages in the cut-out.

In some preferred embodiments, the lock element is able to move radially out of the locked engagement at the end of the dispensing movement so that the driving spring and return spring are coupled with one another, and the return spring has a stronger spring force than the driving spring relaxed due to the dispensing movement, so that the driving spring can be tensed by the return spring. The coupling for the retracting movement is brought about by removing the device from the injection site because the operating sleeve is forced in the distal direction by the force of a separate return spring, as a result of which the lock element is moved out of the cut-out of the operating sleeve. In some preferred embodiments, the lock element can not be moved out of engagement with the operating sleeve while the product is being dispensed. This can be achieved due to the fact that when the product is being dispensed, the plunger rod slides past the lock element so that the lock element is blocked by the external circumferential surface of the plunger rod and is not able to snap out of the engagement with the operating sleeve. The plunger rod has an orifice or the length of the plunger rod is dimensioned so that the lock element can be moved out of engagement with the operating sleeve at the end of dispensing the product.

In some preferred embodiments, the lock element is designed so that it is pushed out of engagement with the operating sleeve as the operating sleeve moves in the distal direction.

In some preferred embodiments, an injection device in accordance with the present invention may have a snapper element which is latched to an element secured to the housing or to the switch sleeve in an axially fixed arrangement once the injection needle has been retracted, and the snapper element and the lock element are disposed on the function sleeve. In some preferred embodiments, the product container and the lock element are connected to one another in an axially fixed arrangement so that they can be moved along the longitudinal axis of the injection device as a single part.

The present invention further relates to a method of extracting and retracting an injection needle carried generally on or at the distal end of an injection device, wherein a product is dispensed in the extracted state, a tensed driving spring partially relaxes and, as it does so, tenses a return spring coupled with the driving spring, the driving spring continues to relax so that product is dispensed and the tensed return spring relaxes and thus tenses the driving spring coupled with the return spring. The method encompasses the fact that the driving spring and return spring are uncoupled while product is being dispensed.

BRIEF DESCRIPTION OF THE DRAWINGS

FIGS. 1a and 1b are sectional diagrams of an embodiment of an injection device in accordance with the present invention, fitted with a cap, FIG. 1b showing a view rotated 90° about the longitudinal axis compared with FIG. 1a.

FIGS. 2a and 2b are sectional diagrams showing the injection device of FIGS. 1a and 1b with a cap removed, FIG. 2b showing a view rotated 90° about the longitudinal axis compared with FIG. 2a.

FIGS. 3a and 3b are sectional diagrams showing the injection device of FIGS. 1a and 1b in an activated state, FIG. 3b showing a view rotated by 90° about the longitudinal axis compared with FIG. 3a.

FIGS. 4a and 4b are sectional diagrams showing the injection device of FIGS. 1a and 1b in a triggered state, FIG. 4b showing a view rotated by 90° about the longitudinal axis compared with FIG. 4a.

FIGS. 5a and 5b are sectional diagrams showing the injection device of FIGS. 1a and 1b in a piercing state, FIG. 5b showing a view rotated by 90° about the longitudinal axis compared with FIG. 5a.

FIGS. 6a and 6b are sectional diagrams showing the injection device of FIGS. 1a and 1b in a dispensed state, FIG. 6b showing a view rotated 90° about the longitudinal axis compared with FIG. 6a.

FIGS. 7a and 7b are sectional diagrams showing the injection device of FIGS. 1a and 1b in a state in which the injection device has emitted a clicking noise to signal the end of dispensing, FIG. 7b showing a view rotated 90° about the longitudinal axis compared with FIG. 7a.

FIGS. 8a and 8b are sectional diagrams showing the injection device of FIGS. 1a and 1b in a situation where retraction of the injection needle has been activated, FIG. 8b showing a view rotated 90° about the longitudinal axis compared with FIG. 8a.

FIGS. 9a and 9b are sectional diagrams showing the injection device of FIGS. 1a and 1b in a final state, FIG. 9b showing a view rotated 90° about the longitudinal axis compared with FIG. 9a.

FIG. 10 is a sectional diagram showing the signalling unit illustrated in FIGS. 1 to 9.

FIG. 11 is a perspective view of the signalling unit illustrated in FIG. 10.

DETAILED DESCRIPTION

Figure 2A:
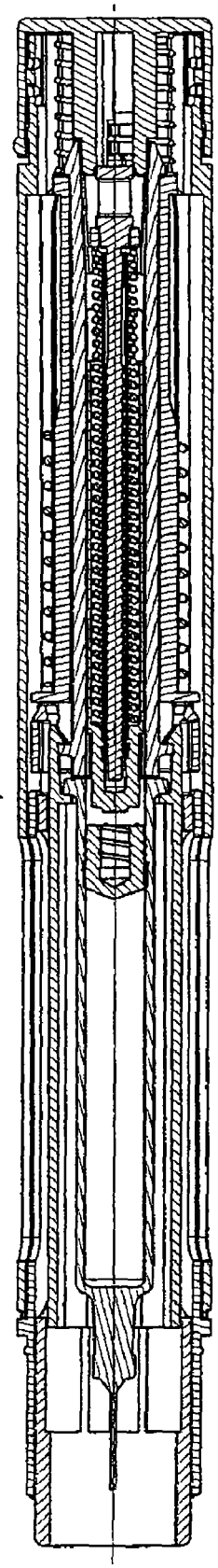

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless stated otherwise, positional terms (e.g., up, down, front, rear, distal, proximal, etc.) are descriptive not limiting. Same reference numbers are used to denote same parts or components.

FIGS. 1a through 9b illustrate an exemplary preferred embodiment of an injection device in accordance with the present invention. Turning specifically to FIGS. 1a and 1b, the injection device comprises a housing 1, with a proximal housing part 1a and a distal housing part 1b connected to the proximal housing part by a catch connection 1c so as to be axially fixed. The catch connection 1c comprises a window associated with or contained in the proximal housing part. An elastic tongue formed on the distal housing part 1b snaps into the window.

Accommodated in the housing 1 is a product container 2, on the distal (front or forward) end of which is an injection needle 4 for dispensing a liquid product contained in the product container 2. At the proximal (rear) end, the product container 2 has a displaceable plunger 3, the movement of which relative to the product container 2 and in the direction of the injection needle 4 causes product to be dispensed. The movement may be thought of and/or referred to as a dispensing movement. The product container 2 is accommodated in the device so that it is able to move in the distal direction so that the injection needle 4 extends out beyond the distal end of the injection device. This movement may be thought of and/or referred to as a piercing movement. The product container 2 is connected to a holder 10 for the product container 2 in an axially fixed arrangement. The housing 1, and its distal and proximal housing parts 1a, 1b, have a viewing window 12 through which the user of the injection device can see the product container 2. The holder 10 surrounds the product container 2 in a sleeve shape and either has a viewing window itself or, as in this example, is made from a transparent material to expose the view onto the container 2. The product container 2 is connected in an axially fixed arrangement by a clamp to a function sleeve 11 disposed proximally of it at the proximal end of the holder 10. At its proximal end, the product container 2 has a radially projecting collar, which is gripped by the clamp. At its distal end, the function sleeve 11 likewise has a radially projecting collar, which is also enclosed by the clamp. Accordingly, the product container 10, function sleeve 11 and holder 10 are connected to one another in an axially fixed arrangement so that they are able to move as a single part. This combination may be thought of and referred to herein as a drive structure.

The function sleeve 11 surrounds a plunger rod 5 which is able to act on the plunger 3 to dispense product. The plunger rod 5 has a sleeve-shaped part which surrounds a driving spring 6 and the driving spring 6 is supported distally on the plunger rod 5 and proximally on a switch sleeve 8, e.g. to a socket 8a disposed on it.

Adjoining the plunger rod 5 is a signalling unit, by which at least one or, in some preferred embodiments at least three or more, haptic and/or acoustic signals can be generated for the piercing operation and/or the dispensing operation. The signalling unit comprises a catch rod 23 connected to the switch sleeve 8 and a locating sleeve 22 surrounding the catch rod 23 and connected, in particular latched, in an axially fixed arrangement to the plunger rod 5. The locating sleeve 22 has a locating element 26 which engages in a groove 27 of the catch rod 23. At its proximal end, the catch rod 23 has a head 24, which is able to move in the proximal direction in a slide guide 25 formed by the activator element 13. The head engages by its distal end with a socket 8*a* disposed on the switch sleeve 8 and the engagement prevents the head 24 and hence the catch rod 23 from being able to move relative to the switch sleeve 8 in the distal direction. The exact way in which this arrangement operates will be explained later herein with reference to FIGS. 10 and 11, which provide a detailed illustration of the signalling unit illustrated in FIGS. 1 to 9. Alternatively, the signalling unit illustrated in FIGS. 10 and 11 may be replaced by a different signalling unit illustrated in FIGS. 12 to 14 and by yet another signalling unit illustrated in FIGS. 15 and 16. The injection device illustrated in FIGS. 1 to 9 does not have to undergo any major modification to this end.

When the injection device is in the initial state illustrated in FIGS. 1*a* and 1*b*, the driving spring 6 is tensed so that the needle 4 and the drive structure are advanced forward for a piercing movement and can push the plunger 3 to effect a dispensing movement. The function sleeve 11 has a lock element 16, on which a shoulder is disposed directed radially inwardly, which, in the initial state, co-operates with a shoulder directed radially outwardly on the distal end of the plunger rod 5 so that the plunger rod 5 is locked, thereby preventing a movement relative to the function sleeve 11. The lock element 16 is held in engagement with the plunger rod 5 by a surface of the switch sleeve 8 pointing or extending radially inwardly. The lock element 16 is elastically connected to the function sleeve 11 by a resilient arm, and may be integral. The resilient arrangement may be designed so that the lock element 16 tends to move radially outward but this is prevented by the surface of the switch sleeve 8 extending radially inward.

At its proximal end, the function sleeve 11 has at least one snapper element 15, which snaps into the switch sleeve 8 in the initial state to prevent any movement of the function sleeve 11 and hence the drive structure. As a result, the pretensed spring 6 is not yet able to relax and the drive structure is not yet able to move in the distal direction.

At the proximal end of its housing 1, the injection device has an activator element 13, which is disposed so that it is axially stationary but can be rotated relative to the housing 1. The activator element 13 houses a return spring 21, which is supported distally on the proximal end of the switch sleeve 8 and proximally on the activator element 13. A purpose of the return spring 21 is to apply a force acting in the distal direction to the switch sleeve 8 and an operating sleeve 9 acting axially on the switch sleeve 8 so that the switch sleeve 8 and operating sleeve 9 are moved in the distal direction. The activator element 13 has an activator lock 14, which engages behind the snapper element 15 when the injection device is in the switching states illustrated in FIGS. 1*a*, 1*b*, 2*a* and 2*b* so that the snapper element 15 is blocked or locked and is not able to move out of engagement with the switch sleeve 8. This advantageously prevents the injection device from being inadvertently triggered. The activator lock can be moved out of engagement with the snapper element 15 by turning the activator element 13 by 90° relative to the housing 1, for example.

A return spring 7 acting in the longitudinal direction of the device is distally supported on the switch sleeve 8 and proximally supported on the function sleeve 11. As illustrated in this example, the return spring 7 surrounds the switch sleeve 8 and the function sleeve 11. The return spring 7 is proximally supported on a collar 11*a* disposed on the function sleeve 11, which extends radially outwardly through an aperture provided in the switch sleeve 8. In certain switch positions therefore, the return spring 7 is able to cause a relative movement between the switch sleeve 8 and function sleeve 11. The return spring 7 is a compression spring which is able to move the function sleeve 11 in the proximal direction relative to the switch sleeve 8. The return spring 7 is not pre-tensioned or is tensioned with only a slight pre-tensioning force. For example, when the injection device is in the state illustrated in FIGS. 1*a* and 1*b*, the pre-tensioning force of the return spring 7 is lower than the pre-tensioning force of the driving spring 6.

Disposed distally of the switch sleeve 8 is the operating sleeve 9 which is able to move relative to the housing 1. The switch sleeve 8 and the operating sleeve 9 are mutually able to apply a pressing force to one another, e.g. latch or connect with one another, thereby pushing one another. To prevent the view onto the product container 2 from being blocked by the operating sleeve 9, the operating sleeve 9 also has a window in the region of the window 12. Alternatively, the operating sleeve 9 may be made from a transparent material. When the return spring 21 is in the initial state, the operating sleeve 9 is pushed forward by the return spring 21 via the switch sleeve 8 distally beyond the distal end of the housing 1. The distal end of the operating sleeve 9 is used for positioning on an injection site of a patient.

The holder 10 has a switch cam 17, which engages in a cut-out 18 of the operating sleeve 9, which may be provided in the form of an aperture as illustrated in this example. The switch cam 17 is elastically connected, integrally, to the holder 10 by a resilient arm, for example. The switch cam 17 is biased so that it tends to engage in the cut-out 18 or move radially outward. The switch cam 17 projecting radially outwardly from the holder 10 has an oblique surface distally, which therefore also co-operates in pushing the switch cam 17 out of engagement with the cut-out 18. Proximally, the switch cam 17 also has a transversely extending stop surface, e.g. perpendicular to the longitudinal direction, which is able to make axial contact with the proximal boundary of the cut-out 18, as a result of which the switch cam 17 is not able to be moved out of the cut-out 18.

The operating sleeve 9 has an axial stop 19, with which the distal end of the holder 10 is able to make contact at the end of the piercing movement.

Figure 2B:
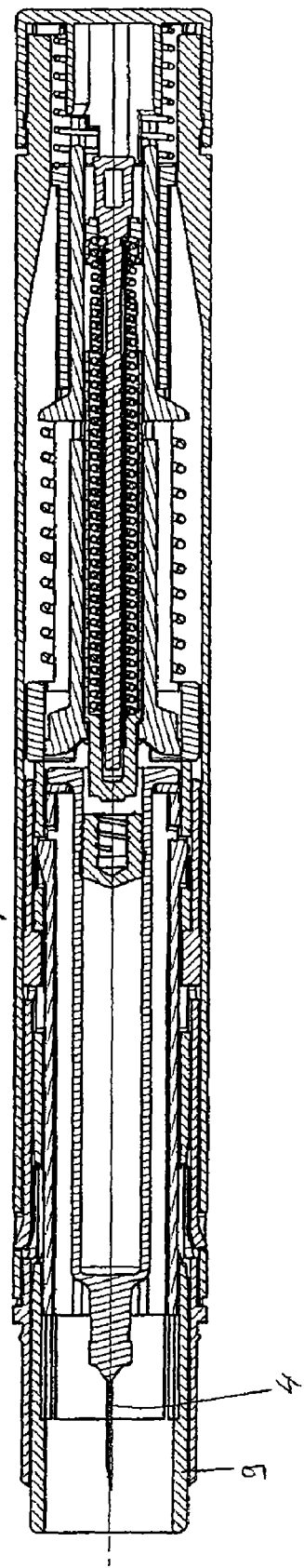

As illustrated in FIGS. 1*a* and 1*b*, the distal end of the injection device is fitted with a cap 32, which protects the interior of the injection device from dirt and keeps the needle 4 sterile. The cap 32 is removed prior to using the injection device so that the needle 4 and the operating sleeve 9 are exposed, as illustrated in FIGS. 2*a* and 2*b*. The state of the injection device illustrated in FIGS. 2*a* and 2*b* differs from the state illustrated in FIGS. 1*a* and 1*b* solely due to the fact that the cap 32 has been removed.

The force exerted on the injection device when the needle cap 32 is pulled off is transmitted via the holder 10 to the function sleeve 11, from where it is transmitted via the snapper 15 to the switch sleeve 8, which is supported on the operating sleeve 9. The operating sleeve 9 is in turn latched to the housing 1 via a projection 1*d* disposed on the distal housing part 1 so that the action of pulling the cap 32 off the injection device does not have an undesired effect on the mechanism.

In the switch state illustrated in FIGS. 2*a* and 2*b*, the operating sleeve 9 can not or can only very slightly be pushed into the distal end of the injection device because this sliding movement is transmitted via the switch sleeve 8 to the snapper 15 and the snapper 15 is prevented from moving in the proximal direction by the activator element 13.

Figure 3A:
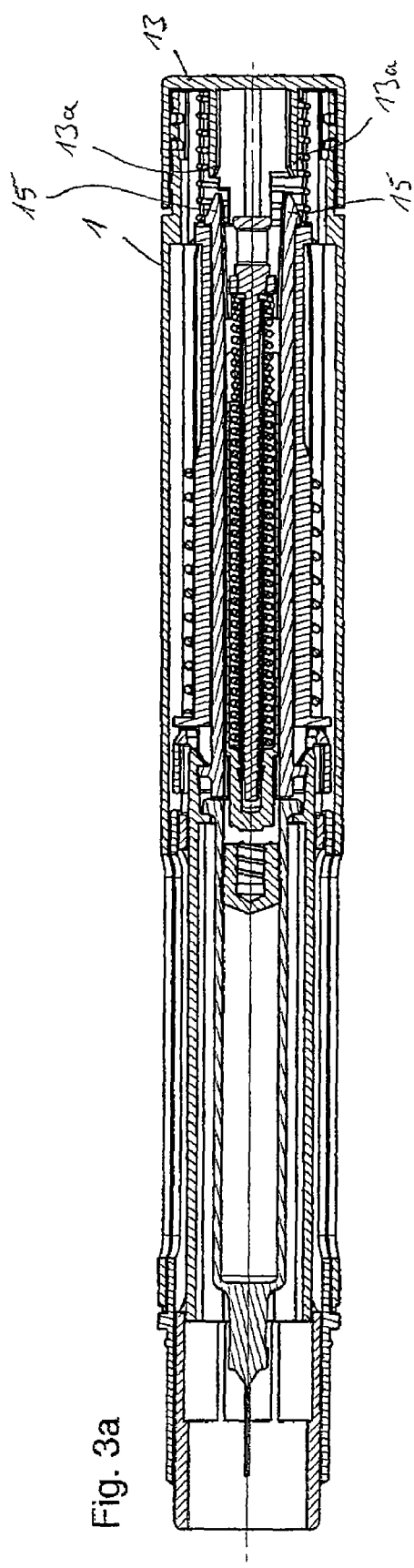
Figure 3B:
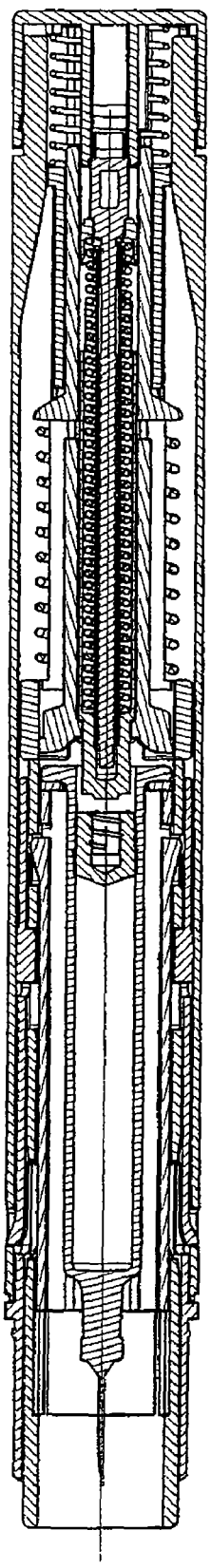

The injection device is illustrated in an activated state in FIGS. 3a and 3b, i.e. the injection device can be triggered. The injection device is activated or unlocked by a rotating movement of the activator element 13, e.g. by 90°. As this happens, the snapper elements 15 are released to permit a movement directed radially inward due to the fact that the activator lock 14 is moved out of engagement with the snapper elements 15, e.g. rotated. Consequently, there is space for the snapper elements 15 to be deflected inward. Like the snapper element 15, the activator element 13 has an activator cam 13a, which is moved into a position axially flush with the snapper element 15 by the rotating movement of the activator element 13. Proximally, the snapper element 15 and, distally, the activator cam 13a disposed proximally of it have a contour which can deflect the snapper element 15 radially inwardly as the snapper element 15 moves into engagement with the activator cam 13. In this example, the contours are two oblique planes extending toward one another.

To trigger the injection device, the user of the device places it with the distal end on the injection site, which typically has been disinfected beforehand. As a result, the operating sleeve 9 is moved in the proximal direction relative to the housing 1, until the distal end of the operating sleeve 9 is more or less flush with the distal end of the distal housing part 1b. Due to the movement of the operating sleeve 9, the switch sleeve 8 is also slaved in the proximal direction, causing the snappers 15 to be pushed by the activator cam 13a radially inwardly out of engagement with the switch sleeve 8. As the operating sleeve 9 moves in the distal direction, the elements of the drive structure are also moved in the proximal direction, as long as the snapper elements 15 are snapped into the switch sleeve 8. Since the plunger rod 5 is in a locked engagement with the function sleeve 11, the plunger rod 5 is also moved in the proximal direction. The signalling unit accommodated in the plunger rod 5 is likewise moved in the proximal direction. The head 24 disposed proximally on the catch rod 23 is able to slide along the guide 25 formed by the activator element 13.

Since no relative movement can yet take place between the activator sleeve 11 and the switch sleeve 8 during this movement, neither the return spring 7 nor the driving spring 6 are tensed or relaxed.

The force which the user of the device must apply to the housing 1 to push the operating sleeve 9 in the proximal direction is determined by the force of the return spring 21 against which the switch sleeve 8 and the operating sleeve 9 are moved. In some embodiments, the spring 21 is a compression spring and is made from a plastic material. Alternatively, it would naturally also be possible to use springs made from spring steel material or some other spring material. The activator element 13 is axially secured to the housing 1 by a snap ring connection to the housing. If the operating sleeve 9 is not pushed far enough toward the injection site and the snapper elements 15 are not released from the engagement with the switch sleeve 8, the trigger mechanism, e.g. the switch sleeve 8 and the operating sleeve 9, are re-set by the return spring 21 when the injection device is moved away from the injection site.

As may be seen from FIG. 4b, a lock window 20 is formed due to the movement of the operating sleeve 9 in the proximal direction, which is bounded distally by the housing 1, e.g. the projection 1d, and proximally by the operating sleeve 9. Since no relative movement can yet take place between the drive structure and the operating sleeve 9 as the operating sleeve 9 is moving in the proximal direction, the switch cam 17 remains in the cut-out 18.

Once the snappers 15 have been released from the engagement with the switch sleeve 8, the driving spring 6 is able to relax to a certain extent, as a result of which the drive structure is pushed in the distal direction. This being the case, the injection needle 4 moves beyond the distal end of the injection device. Since the function sleeve 11 moves relative to the switch sleeve 8 during this piercing movement, the return spring 7 is compressed, i.e. tensed. The spring force of the driving spring 6 is stronger than the spring force of the return spring 7 during the entire piercing operation, i.e. including at the start and at the end of the piecing operation. An advantage of this is that the piercing force is reduced, for example, which prevents the injection device from damage.

Figure 5A:
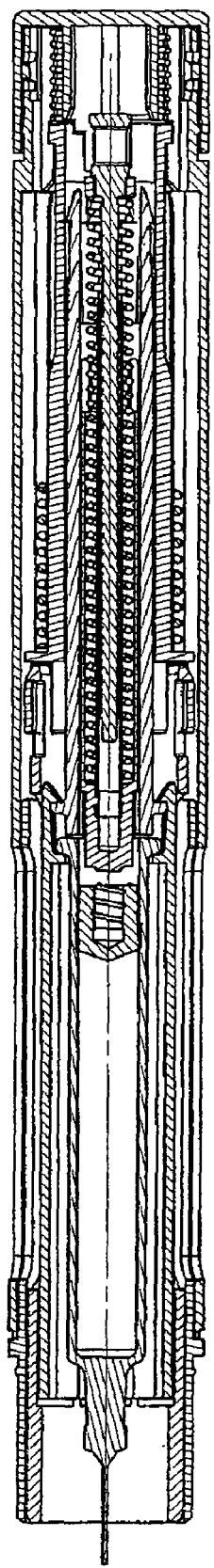
Figure 5B:
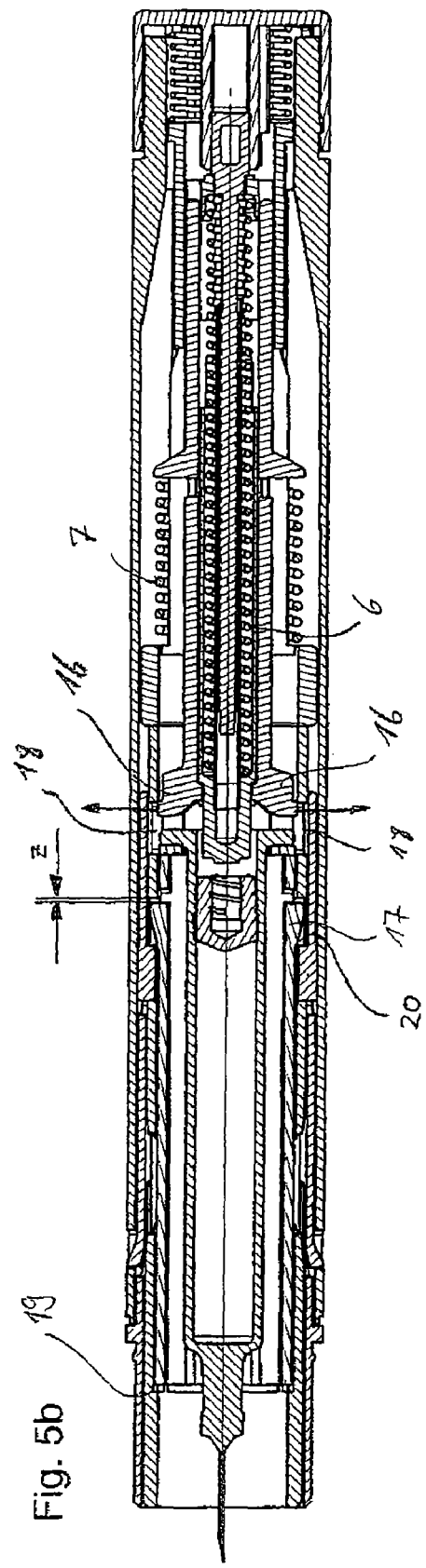

As may be seen from FIGS. 5a and 5b illustrating the situation at the end of the piercing operation, the lock element 16 engages in the cut-out 18 by a movement directed radially outwardly, as indicated by the arrows in FIG. 5b. To improve this locating action, the lock element 16 has a projection directed radially outwardy. The lock element 16 fulfils a dual function. As the lock element 16 latches in the cut-out 18, the lock element 16 is simultaneously released from the plunger rod 5 by the movement directed radially outward, releasing the latter for a dispensing movement. Conversely, the movement of the drive structure in the axial direction, in the proximal direction, is blocked. As a result of this operation, the driving spring 6 is uncoupled from the return spring 7, i.e. the driving spring 6 has no effect on the tensioning of the return spring 7 in this state. A dispensing movement then follows, during which a clicking noise is emitted at constant times by the signalling unit, which is perceptible to the user of the device.

No additional force due to the piercing operation can be felt by the user of the device. This is absorbed by the snapping action between the operating sleeve 9 and the switch sleeve 8 and is not transmitted to the housing. The force for the piercing operation is directed via the function sleeve 11 to the collar of the product container 2. The piercing operation is therefore forcibly controlled because the function sleeve 11 drives the product container 2 forward until the end of dispensing and the plunger rod 5 is not able to dispense until the lock elements 16 have located in the cut-outs 18. The piercing movement is stopped by the stop 19 on the operating sleeve 9.

During the piercing movement, the switch cam 17 is forced out of the engagement with the cut-out 18 due to its distal design of the distal boundary of the cut-out 18 of the operating sleeve 9 and pushed in the distal direction so that it latches in the lock window 20, as illustrated in FIGS. 5a and 5b. The lock element 16 latched in the cut-out 18 in contact with the proximal boundary or edge of the cut-out 18. Since the lock element 16 and the switch cam 17 are disposed at a defined distance from one another due to their axially fixed arrangement, there is a short distance between the proximal end of the switch cam and the distal end of the lock window 20 when the lock element 16 is engaged by the cut-out, which in this instance is 0.5 to 1 mm, for example. As explained in more detail below, this distance is used to produce a haptic or acoustic signal which is intended to indicate that the product has been fully dispensed. The short distance z results from the difference between the distance existing between the stop surface of the switch cam 17 pointing in the proximal direction and the stop surface pointing in the proximal direction, and the distance of the proximal boundaries of the cut-out 18 and the lock window 20.

Figure 6A:
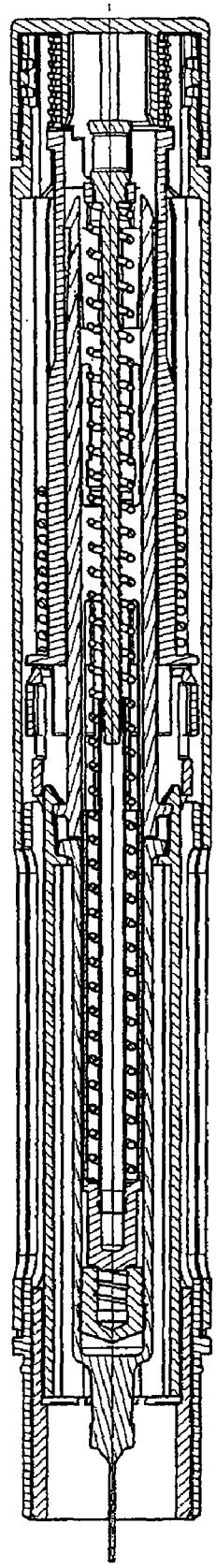
Figure 6B:
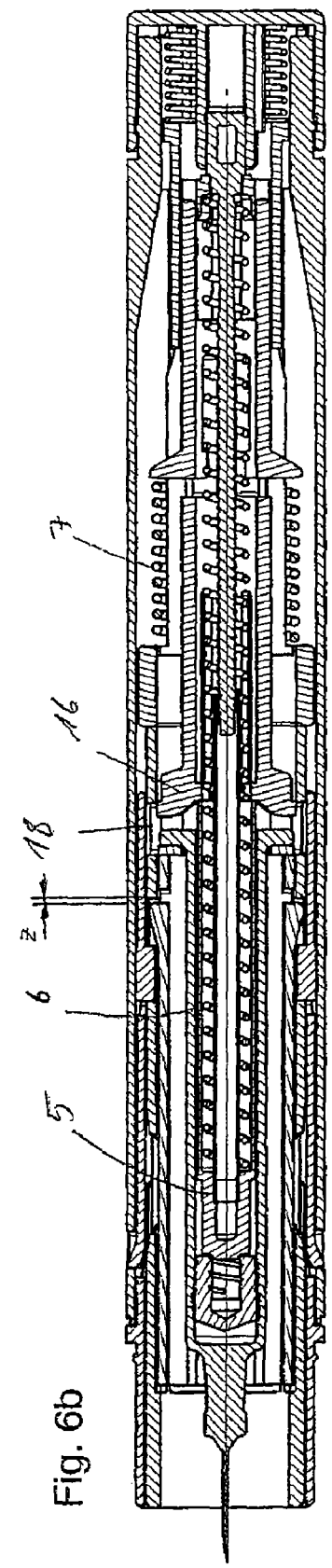

FIGS. 6a and 6b illustrate the injection device in a state in which a product has been dispensed. During dispensing of the product, the external circumferential surface of the sleeve-shaped part of the plunger rod 5 pushes the lock element 16 into the cut-out 18, as a result of which the lock element 16 is locked to prevent it from unlatching from the cut-out 18 while product is being dispensed. The plunger rod 5 may have a cut-out or may be of such a length that when the product has been dispensed, the locking action of the lock element 16 by the external circumferential surface of the plunger rod 5 disappears so that the lock element 16 is able to unlatch from the cut-out 18, as illustrated in FIG. 6b. The unlatching action may be caused by an elastically biased arrangement of the lock element 16 or due to the geometry of the lock element 16, which causes the lock element 16 to be pushed out of the cut-out 18.

Figure 7A:
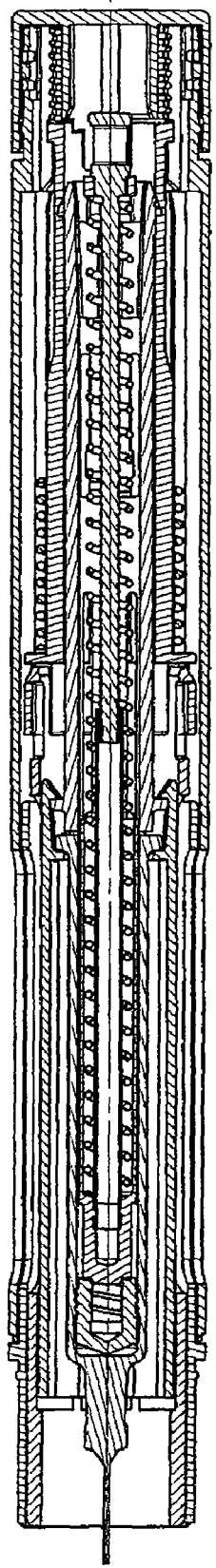
Figure 7B:
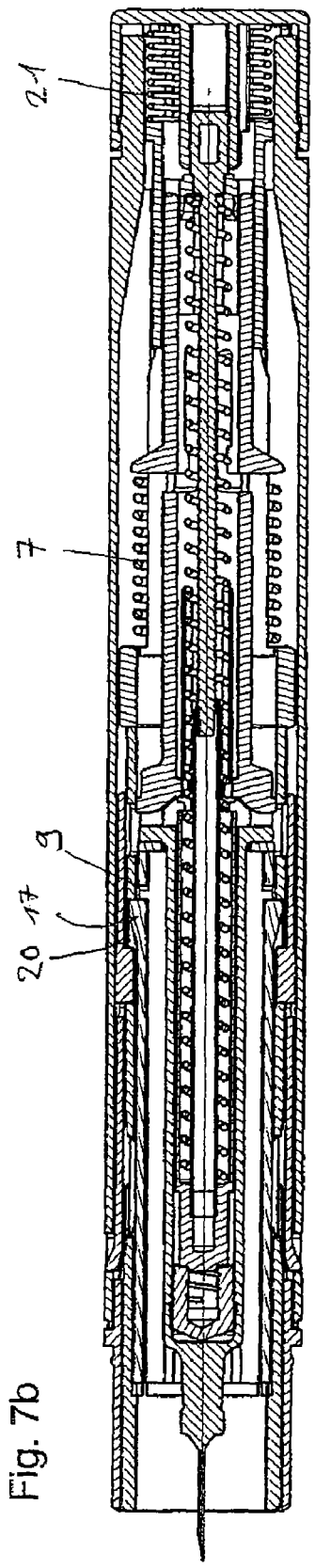
Figure 8A:
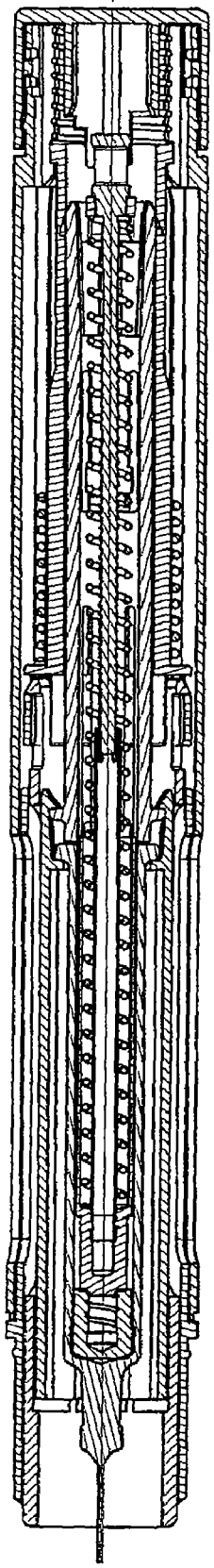
Figure 8B:
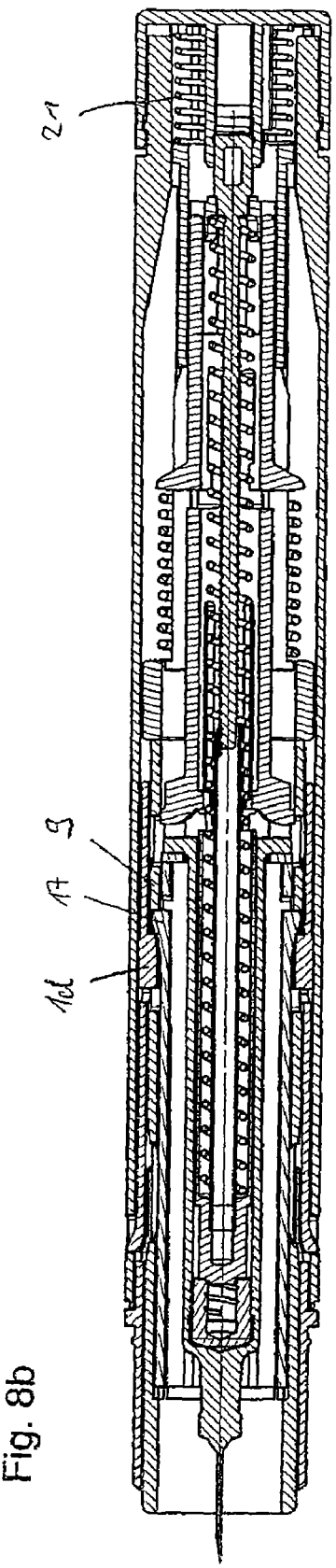

At the end of dispensing the product, the driving spring 6 has further relaxed, while the tensioning of the tensed return spring 7 remains constant. The spring force of the driving spring 6 is now weaker than the spring force of the tensed return spring 7. When the engagement of the lock element 16 with the cut-out 18 is released, the return spring 7 and driving spring 6 are coupled with one another again. As illustrated in FIGS. 7a and 7b, this coupling causes the short distance z (see FIGS. 5b and 6b) to disappear because the drive structure, e.g. the switch cam 17 to be moved by its proximal end abruptly onto the distal end of the lock window 20. As the switch cam 17 makes contact, a haptic and/or acoustic signal is generated. This movement by the short distance z does not yet cause the needle 4 to be completely retracted from the patient, however. The patient or user of the device can now wait any time until the needle has been completely pulled out of the patient because he or she can selectively initiate the automatic retraction of the needle of the device.

A complete movement of the needle into the distal end of the housing 1 is still not possible because, as may be seen from FIG. 7b, the switch cam 17 is engaged with the lock window 20 and is thus preventing the spring 7 from relaxing. To release or activate retraction of the needle 4, the user of the device merely has to remove the latter from the injection site. As a result, the return spring 21 is able to move the operating sleeve 9 in the distal direction via the switch sleeve 8. As this happens, the drive structure is stationary relative to the operating sleeve 9 so that the switch cam 17 is pushed radially inward out of the lock window 20, due to its distal shape, driven by the spring 21 connected to the operating sleeve 9 by the projection 1d. As soon as the switch cam 17 is pushed inward, the needle 4 is free to retract. Also as a result of the releasing action, the return spring 7 is released for a retracting movement. Due to the stronger spring force of the pre-tensed return spring 7, the entire drive structure is pushed in the proximal direction. As a result, the spring 6 is tensed again and the spring force of the return spring 7 is stronger than the spring force of the driving spring 6 during the entire retraction operation, i.e. including up to the end of the retracting movement.

FIGS. 9a and 9b illustrate the injection device in a final state. In this state, the injection device has again the same dimensions it had at the start. Consequently, the cap 32 can be fitted again and the injection device disposed of. In the end position, the needle has been completely retracted into the distal end of the device. The snapper element 15 is latched to the switch sleeve 8 again, as at the start. However, it is not possible to trigger the injection device again because a pre-tensioned driving spring 6 would be necessary to do this, as illustrated in FIG. 1a, for example.

FIGS. 10 and 11 provide detailed illustrations of the signalling unit illustrated in FIGS. 1 to 9. The catch rod 23 has a catch 30 comprising a plurality of catch elements 31, disposed along the longitudinal direction at distances which decrease in steps. These distances become smaller on the basis of the easing spring force. The catch rod is connected to the switch sleeve 8 (see FIG. 1, for example) by its proximal end, e.g. by its head, so as to be axially fixed in at least one direction. The catch rod 23 is surrounded by a catch sleeve 22, which is connected by the distal end to the driving spring 6 or/and to the distal end region of the plunger rod 5. The locating sleeve has a locating element 26 which engages in an annular groove 27. The locating element 26 engages in the groove 27 in the initial position. During the driving movement which takes place until piercing, i.e. during the piercing movement, the locating element unlatches from the groove 27 and moves across a first portion of the catch rod as far as the start of the plurality of catch elements 31. The first part has no other catch element but is of a cylindrical shape or tapers so that no signals are emitted during the piercing movement. In principle, embodiments are possible where this might be an advantage. The length of the first portion is dimensioned so that the locating element 26 has moved completely past the first portion once the piercing movement has ended. At the start of the dispensing movement, the rod 23 and sleeve 22 are pulled even further apart so that the locating element 26 moves across the second portion, i.e. the portion with the catch element 31, thereby moving past the respective catch elements 31. On moving past each of the catch elements, a short clicking signal is emitted. The time intervals from one clicking signal to the next one are constant, although the easing spring force reduces the speed of the locating element 26 as the distance traveled increases. In some embodiments, the distances from one catch element to the next decrease with the spring travel. This makes allowance for the changing speed.

On the side radially opposite that on which the locating element 26 is disposed, another locating element 26 may be provided, for example. In some embodiments, another locating element 26 may not be present, but only a support formed by the sleeve wall which acts as a thrust bearing.

Figure 12:
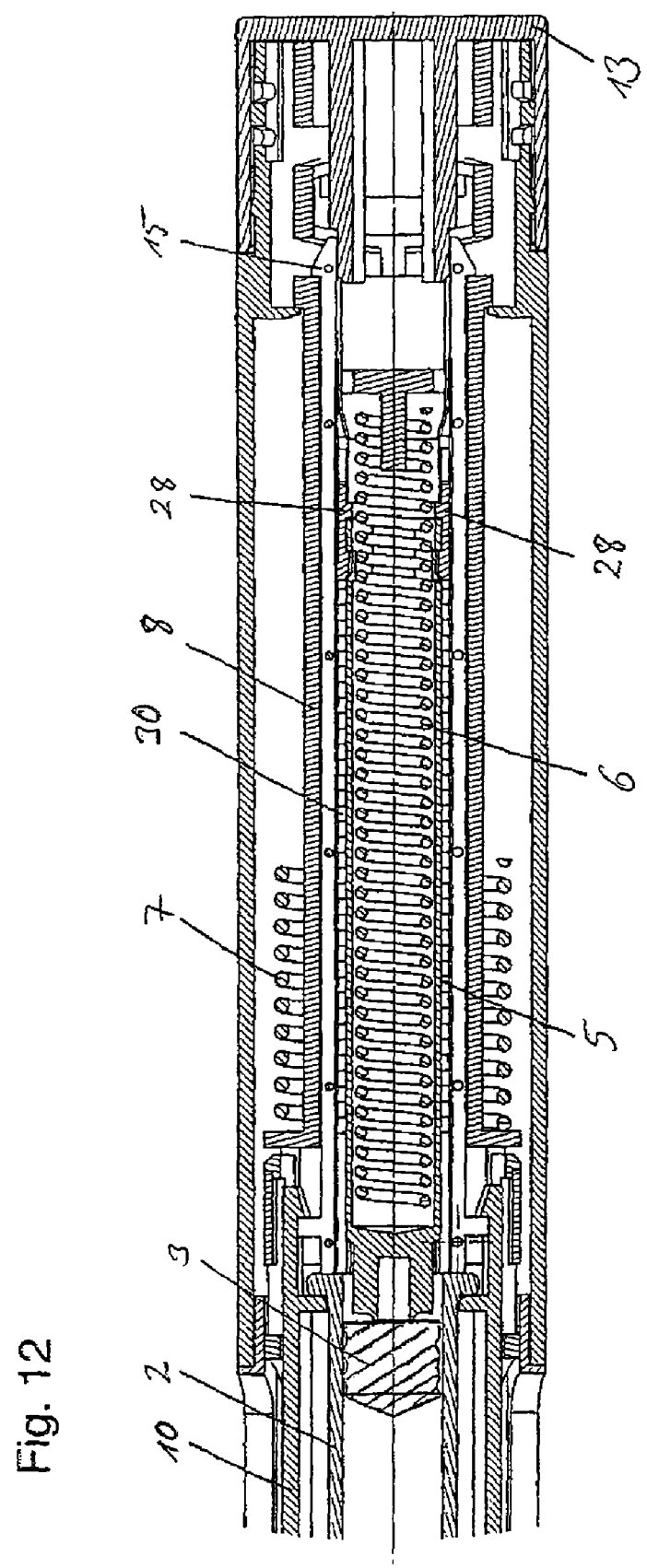
FIG. 12 illustrates an embodiment of an injection device in accordance with the present invention with a different embodiment of a signalling unit.
Figures 13, 14:
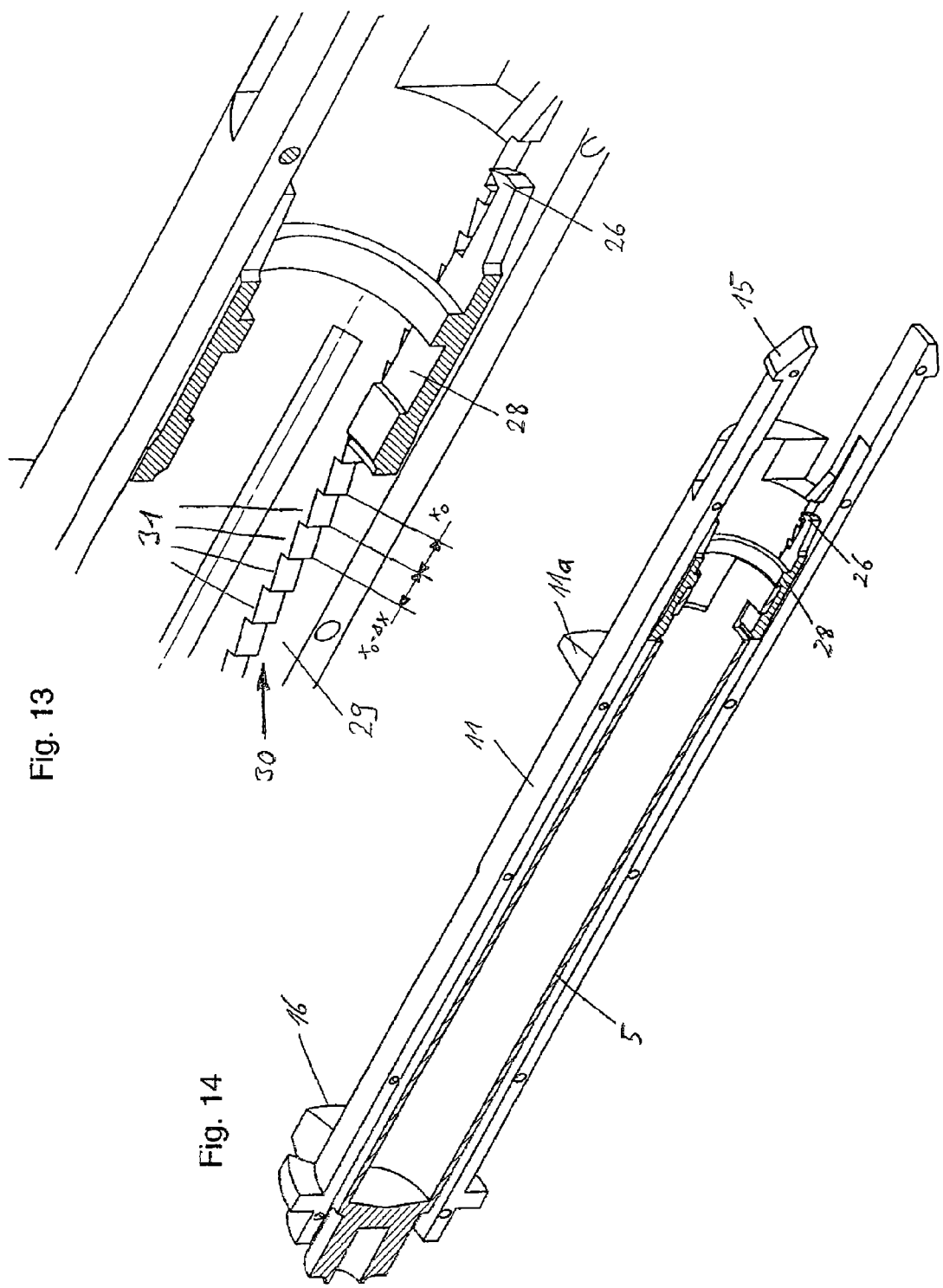
FIG. 13 is a sectional diagram showing the signalling unit illustrated in FIG. 12.
FIG. 14 is another sectional diagram showing the signalling unit illustrated in FIG. 12.

FIGS. 12 to 14 illustrate an alternative embodiment of the signalling unit for the injection device illustrated in FIGS. 1 to 9. The catch 30 is disposed in a groove 29, against its flank. The catch elements 31 project out from the groove flank in the circumferential direction. Disposed in the groove 29 is an axially displaceable carriage 28 which is coupled with the plunger rod 5 in an axially fixed arrangement. During the dispensing movement, the carriage 28 is taken along by the plunger rod 5, as a result of which the locating element 26 resiliently arranged on the carriage 28 travels across the individual catch elements 31 of the catch 30. Here too, the catch elements 31 are respectively disposed at distances apart from one another which permit an emission of signals at constant times making allowance for the changing force of the driving spring. The distance of the sawteeth is selected so that the individual clicks occur at identical time intervals even though the carriage 28 together with the plunger rod 5 has a slower dispensing speed at the end of dispensing than at the start.

Figure 16:
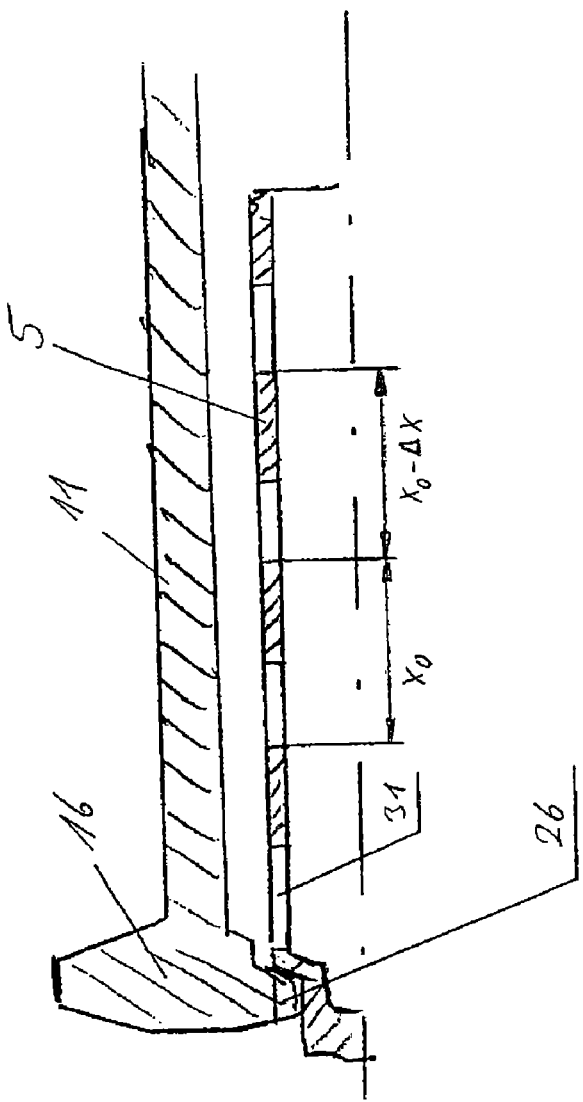
FIGS. 15 and 16 illustrate another embodiment of a signalling unit in accordance with the present invention.
Figure 15:
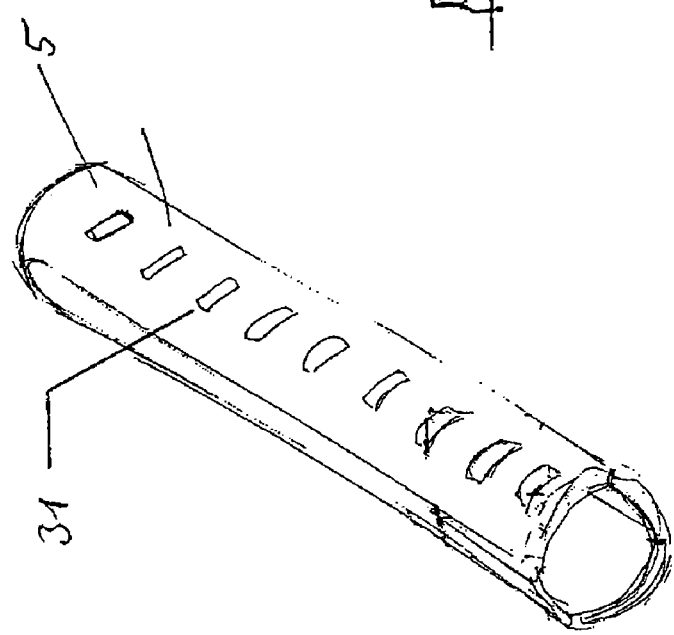

FIGS. 15 and 16 illustrate another embodiment of the signalling unit in which the catch 30 is provided in the form of cut-outs, e.g. windows, which are also disposed on the plunger rod 5 at varying distances. The locating element 26 is resiliently mounted on the function sleeve 11. During the dispensing movement, the plunger rod 5 and hence the perforated catch 30 is moved along past the locating element 26 which locates or is received in each perforated catch 31 and thus generates the signal. An advantage of this embodiment is that the locating element 26 is formed by the lock element 16 which means that this embodiment requires a small number of parts.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for injecting a substance, comprising:
   a thrust spring that moves an injection needle carried by the injection device from an initial position to an insertion position and causes the substance to be injected, and
   a return spring that moves the injection needle from the insertion position into the injection device counter to the force of the thrust spring, wherein the return spring is decoupled from the thrust spring at the end of a piercing movement, such that the thrust spring has no effect on the return spring during dispensing of the substance through the injection needle, wherein
   the spring force of the return spring for retracting the injection needle is stronger than the spring force of the thrust spring and the spring force of the thrust spring for moving the needle from the initial position to the insertion position is stronger than the spring force of the return spring.

2. An injection device for injecting a substance, the injection device comprising:
   a) a driving spring, by which an injection needle can be moved forward out of the distal end of the injection device from an initial position to a piercing position and by which a product can be dispensed from a product container due to a dispensing movement;
   b) a return spring, by which the injection needle can be retracted from the piercing position into the distal end of the injection device against the force of the driving spring; and
   c) a function sleeve comprising one or more lock elements; wherein
   d) the driving spring is coupled with the return spring via the function sleeve during a piercing movement, and wherein during the piercing movement the driving spring relaxes and thus tenses the return spring; wherein
   e) at the end of the piercing movement a dispensing movement follows such that the driving spring is uncoupled from the return spring and has no effect on the tensioning of the return spring; and wherein
   f) during the retraction of the injection needle the driving spring is again coupled with the return spring via the function sleeve and the return spring relaxes and thus tenses the driving spring.

3. The injection device as claimed in claim 2, wherein the driving spring can be tensed by the return spring for retracting the injection needle and the return spring can be tensed by the driving spring for driving the injection needle from the initial position into the piercing position.

4. The injection device as claimed in claim 2, wherein the spring force of the return spring for retracting the injection needle is stronger than the spring force of the driving spring and the spring force of the driving spring for the piercing action of the injection needle is stronger than the spring force of the return spring.

5. The injection device as claimed in claim 2, further comprising a lock element which can be moved radially into a cut-out in a locked engagement to uncouple the driving spring and return spring, as a result of which the injection needle is axially fixed and the return spring is retained in a tensed state.

6. The injection device as claimed in claim 5, wherein the lock element can be moved radially out of the locked engagement at the end of the dispensing movement so that the driving spring and return spring are coupled with one another, and the return spring has a stronger spring force than the driving spring relaxed due to the dispensing movement, and the driving spring can be tensed by the return spring.

7. The injection device as claimed in claim 5, further comprising a snapper element which latches with one of an element secured to the housing or a switch sleeve so as to be axially fixed after the injection needle has been retracted, the snapper element and the lock element being disposed on a function sleeve of the injection device.

8. The injection device as claimed in claim 5, wherein the product container and the lock element are connected in an axially fixed arrangement so that they are able to move along the longitudinal axis of the injection device as a single part.

9. The injection device as claimed in claim 2, further comprising a lock element which is in a releasable engagement with a plunger rod associated with the injection device, and when the engagement is released, the plunger rod can be driven by the driving spring, can be moved relative to the lock element and can move a plunger in the product container in the direction of an outlet of the product container.

10. The injection device according to claim 2, further comprising a lock element which can be moved radially into a cut-out in a locked engagement to uncouple the driving spring and return spring, as a result of which the injection needle is axially fixed and the return spring is retained in a tensed state, and which is in a releasable engagement with a plunger rod associated with the injection device, and when the engagement is released, the plunger rod, which can be driven by the driving spring, can be moved relative to the lock element and can move a plunger in the product container in the direction of an outlet of the product container.

11. The injection device as claimed in claim 2, wherein the return spring is disposed proximally of the product container.

12. The injection device as claimed in claim 2, further comprising a sleeve-shaped plunger rod, wherein the driving spring is at least partially disposed in the sleeve-shaped plunger rod.

13. The injection device as claimed in claim 2, wherein the injection needle is retracted from the piercing position into the distal end of the injection device against the force of the driving spring by a retracting movement, and wherein the driving spring is coupled with the return spring via the function sleeve during the retracting movement.

14. A method of extending and retracting an injection needle carried at the distal end of an injection device, whereby a product is dispensed from the injection device in an extended state of the needle, the method comprising the steps of
   a) at least partially relaxing a pre-tensioned driving spring and thereby tensioning a return spring coupled with the driving spring during the extending of the needle, b) relaxing the driving spring more without further tensioning the return spring and thereby dispensing the product, and
c) relaxing the tensioned return spring and thereby tensioning the driving spring coupled with the return spring at the end of dispensing the product, wherein
d) the driving spring and return spring are uncoupled at the end of the extending movement and as product is dispensed through the injection needle.

* * * * *